US00PP29288P3

(12) United States Plant Patent
Bacon

(10) Patent No.: US PP29,288 P3
(45) Date of Patent: May 15, 2018

(54) GRAPEVINE PLANT NAMED 'SUGRAFIFTY'

(50) Latin Name: *Vitis vinifera*
Varietal Denomination: Sugrafifty

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 92 days.

(21) Appl. No.: 15/330,453

(22) Filed: Sep. 22, 2016

(65) Prior Publication Data

US 2018/0084685 P1 Mar. 22, 2018

(51) Int. Cl.
*A01H 5/08* (2018.01)

(52) U.S. Cl.
USPC ..... Plt./205
CPC ..... *A01H 5/0812* (2013.01)

(58) Field of Classification Search
USPC ..... Plt./205
See application file for complete search history.

*Primary Examiner* — Anne Marie Grunberg
(74) *Attorney, Agent, or Firm* — Knobbe, Martens, Olson & Bear, LLP

(57) ABSTRACT

A new and distinct variety of grapevine 'Sugrafifty' is characterized by a midseason harvest date, the production of a large-sized, red, broad elliptic berry and a very large bunch size. The berries of 'Sugrafifty' are very firm.

1 Drawing Sheet

Latin name of the genus and species claimed: *Vitis vinifera.*

Variety denomination: 'SUGRAFIFTY'.

BACKGROUND AND SUMMARY OF THE INVENTION

This application relates to the discovery and asexual propagation of a new and distinct variety of grapevine, 'Sugrafifty', as herein described and illustrated. The new variety was first selected as breeder number 'GR377R' by Terry A. Bacon in Wasco, Kern County, Calif. in August 2013. The variety was originated by controlled hybridization.

The new variety 'Sugrafifty' is characterized by a midseason harvest date, the production of a large-sized, red, broad elliptic berry and a very large bunch size. The berries of 'Sugrafifty' are very firm.

The seed parent is the varietal selection 'Sugrathirtyfive' (U.S. Plant Pat. No. 20,491) and the pollen parent is from bulk pollen of several red grapevine varieties. The parent varieties were first crossed in May 2011. The date of first sowing was March 2012, and the date of first flowering was May 2013.

The new variety 'Sugrafifty' was first asexually propagated in December 2013 in Wasco, Kern County, Calif., by Terry A. Bacon using hardwood cuttings.

The new variety 'Sugrafifty' differs from its seed parent 'Sugrathirtyfive' (U.S. Plant Pat. No. 20,491) in that harvest of grapes of the new variety 'Sugrafifty' starts about August 5$^{th}$ compared to about August 28th for 'Sugrathirtyfive'. The new variety 'Sugrafifty' also differs from its seed parent 'Sugrathirtyfive' in that the new variety 'Sugrafifty' has a red berry while 'Sugrathirtyfive' has a green berry.

The new variety has a red berry similar to that of 'Crimson Seedless' (unpatented), 'Sugrathirtyeight' (U.S. Plant Pat. No. 22,431), 'Scarlet Royal' (U.S. Plant Pat. No. 16,229). The beginning of ripening is August 5$^{th}$ for the new variety, compared to September 5th for 'Crimson Seedless', August 10$^{th}$ for 'Sugrathirtyeight', August 25$^{th}$ for 'Scarlet Royal' and July 20th for 'Sugrathirteen' (U.S. Plant Pat. No. 10,434). The new variety also has a broad, elliptic berry shape, compared to an elongated berry shape for both 'Crimson Seedless', 'Sugrathirteen' and 'Scarlet Royal'. The new variety 'Sugrafifty' differs from 'Sugrathirtyeight', which has an oval shape. The new variety 'Sugrafifty' has a rudimentary seed similar to 'Crimson Seedless', 'Sugrathirteen' and 'Sugrathirtyeight', but different from 'Scarlet Royal' which has a noticeable seed trace. The new variety 'Sugrafifty' has a larger berry weight than 'Crimson Seedless', 'Sugrathirteen', 'Sugrathirtyeight' and 'Scarlet Royal'. The new variety 'Sugrafifty' has a larger cluster weight than 'Crimson Seedless', 'Sugrathirteen', 'Sugrathirtyeight' and 'Scarlet Royal'.

The new 'Sugrafifty' variety has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafifty'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three year old 'Sugrafifty' plants grown in the vicinity of Wasco, Kern County, Calif. during 2016, and is believed to apply to plants of the variety grown under similar conditions of soil and climate elsewhere.

Vine:

*General*.—(Measurements taken on a three year old plant). Vine Size: Large. Height: Approximately 2.0 m. Width: Approximately 2.5 m. Vigor: Vigorous. Density of foliage: Dense. Productivity: Very productive. Crop load: Approximately 34 kg per vine after thinning. Own root: Yes. Training method: Typically spur pruned leaving 2 bud spurs. Resistance: Neither resistance nor susceptibility to diseases or pests has been observed in this variety.

*Trunk*.—Shape: Stocky. Diameter: Approximately 7.5 cm (at 30 cm above the soil line). Straps: Short. Surface texture: Medium shaggy. Inner and Outer bark color: Inner bark about Medium Greyed-Orange 166D and Light Greyed-Green 198D in outer bark.

Shoots:

*Young shoot*.—Form of tip: Half open. Intensity of anthocyanin coloration of tip: Absent or very weak. Density of prostrate hairs on tip: Absent or very sparse. Density of erect hairs on tip: Absent or very sparse. Color: About Medium Yellow-Green 144B.

*Woody shoot* (*observations made in the middle third of shoot*).—Attitude before tying: Semi-drooping to drooping. Growth of axillary shoots: Medium strong, mainly 17 to 30 cm. Internode length: Long, Approximately 80 mm to 95 mm. Width at node: Approximately 15 mm. Cross section: Circular. Surface texture: Striated. Main Color: About Light Greyed-Orange 171D. Color of dorsal side of internode: About Light Greyed-Orange 171D. Color of ventral side of internode: About Medium Greyed-Orange 171B. Color of dorsal side of node: About Medium Yellow-Green 146C with Medium Greyed-Orange 171B. Color of ventral side of node: About Medium Yellow-Green 146C with Medium Greyed-Orange 171B. Density of erect hairs on nodes: Absent or Very Sparse. Density of erect hairs on internodes: Absent or Very Sparse. Density of prostrate hairs on internodes: Absent or Very Sparse. Density of prostrate hairs on nodes: Absent or Very Sparse.

*Tendrils*.—Distribution on the shoot at full flowering: Discontinuous. Thickness: Approximately 4 mm. Color: About Light Yellow-Green 148D in midsummer. Form: Bifurcated. Number of consecutive tendrils: Up to 2. Length of tendril: Medium, approximately 16.5 cm.

Leaves:

*Young leaves*.—Color of upper surface of first 4 distal unfolded leaves: About Medium Green 138B. Average intensity of anthocyanin coloration of six distal leaves prior to flowering: Absent. Density of prostrate hairs between veins at lower surface of 4th distal unfolded leaf: Absent or very sparse. Density of erect hairs between veins at lower surface of 4th distal unfolded leaf: Absent or very sparse. Density of prostrate hairs on veins at lower surface of 4th distal unfolded leaf: Absent or very sparse. Density of erect hairs on veins at lower surface of 4th distal unfolded leaf: Absent or very sparse.

*Mature leaves* (*observations made in the middle third of shoot*).—Average length: Large, approximately 110 mm. Average width: Large, approximately 160 mm. Shape of blade: Pentagonal. Number of lobes: Approximately 5. Mature leaf profile: Undulate. Blistering surface of blade upper surface: Absent or very weak. Leaf blade tip: In the plane of the leaf. Undulation of margin: Slight. Thickness: Average — typical of *Vitis vinifera* species. Overall shape of teeth: Mixture of both sides straight and both sides convex. Length of teeth: Medium, ranging from about 3 mm to 10 mm. Ratio length/width of teeth: Variable but usually small. General shape of petiole sinus lobes: Half open. Tooth at petiole sinus: Absent. Petiole sinus limited by veins: Absent. Shape of upper lateral sinus lobes: Open. Depth of upper lateral sinuses: Shallow, approximately 10 mm to 20 mm. Density of prostrate hairs between veins on lower surface of blade: Absent to very sparse. Density of erect hairs between veins on lower surface of blade: Absent to very sparse. Density of prostrate hairs on main veins on lower surface of blade: Absent to very sparse. Density of erect hairs on main veins on lower surface of blade: Absent to very sparse. Density of prostrate hairs on main veins on upper surface of blade: Absent to very sparse. Autumn coloration of leaves: Usually about Medium Yellow-Green 145B with occasional patches of about Dark Greyed-Red 181A.

*Upper leaf surface*.—Color: About Dark Green 141B. Surface texture: Smooth. Surface appearance: Dull. Anthocyanin coloration of main veins: Absent or very sparse.

*Lower leaf surface*.—Color: About Light Green 138C. Surface texture: Smooth. Surface appearance: Dull. Anthocyanin coloration of main veins: Absent or very sparse.

*Petiole*.—Length of petiole: Medium, approximately 80 mm. Diameter: Approximately 4 mm. Length of petiole compared to middle vein: Slightly shorter, 80 mm for the petiole compared to 110 mm for middle vein. Density of prostrate hairs on petiole: Absent. Density of erect hairs on petiole: Absent. Color: About Medium Green 138B, becoming Light Greyed-Red 182D as it ages.

*Buds*.—Shape: Conical. Size: Medium, approximately 3 mm wide×4 mm long. Position: Slightly held out. Bud fruitfulness: Basal, mostly fruitful $3^{rd}$ to $5^{th}$ bud position. Time of bud burst: Medium for area of Wasco, Calif. Approximately March 16th.

Flowers:

*General*.—Flower type: Fully developed stamen and fully developed gynoecium. Position of first flowering node: Usually $4^{th}$ to $5^{th}$ node of current season growth. Number of inflorescences per shoot: Approximately 1 to 2 with an average of about 1.5. Time of full bloom: Medium for area of Wasco, Calif. Approximately April 30th.

Fruit:

*General*.—Ripening period: Midseason, beginning about August 5th with mid-ripe about August 12th. Use: Fresh market. Storage quality: Excellent.

*Cluster*.—Form: Conical, shouldered. Cluster size (peduncle excluded): Large. Cluster length (peduncle excluded): Approximately 24 cm. Cluster width: Approximately 21 cm. Cluster weight: Approximately 850 g. Cluster density: Medium, loose and full. Number of berries: Approximately 100-130.

*Peduncle*.—Length: Medium, approximately 2.2 cm. Diameter: Approximately 6 mm. Lignification of peduncle: Weak. Color: Medium Yellow-Green 146C.

*Berry*.—Size: Very large, natural size averages 9.5 g. Dimensions: Longitudinal axis: Approximately 34 mm. Horizontal axis: Approximately 24 mm. Uniformity of size: Uniform. Shape: Broad elliptic. Cross section: Circular. Skin color (without bloom): About Medium Red 47C. Flesh color: Usually about Light Green 139D near the center and about Green-White 157B around the perimeter beneath the skin. Anthocyanin color of flesh: Absent or very weak. Bloom (cuticular wax): Medium. Pedicel length: Approximately 7 mm. Pedicel thickness: Medium, approximately 1.8 mm. Berry separation from pedicel: Moderately easy. Seed traces: Berries contain 1 to 3 rudimentary soft seed traces per berry. Seed traces are about Medium Greyed-White 156B. Berry firmness: Very firm. Flesh Juiciness: Juicy. Flesh texture: Crisp. Particular flavor: None. Refractometer test: About 19 Brix. Juice pH: About 3.6. Titratable acidity: About 0.49%. Brix:Acid Ratio: Approximately 38.8.

*Skin*.—Skin thickness: Medium, about 175 μm. Skin texture: Smooth. Skin reticulation: Absent. Skin tenacity: Tenacious to flesh. Skin tendency to crack: Low. Skin sensitivity to sunburn: None or very low.

What is claimed is:

1. A new and distinct variety of grapevine as herein illustrated and described.

* * * * *

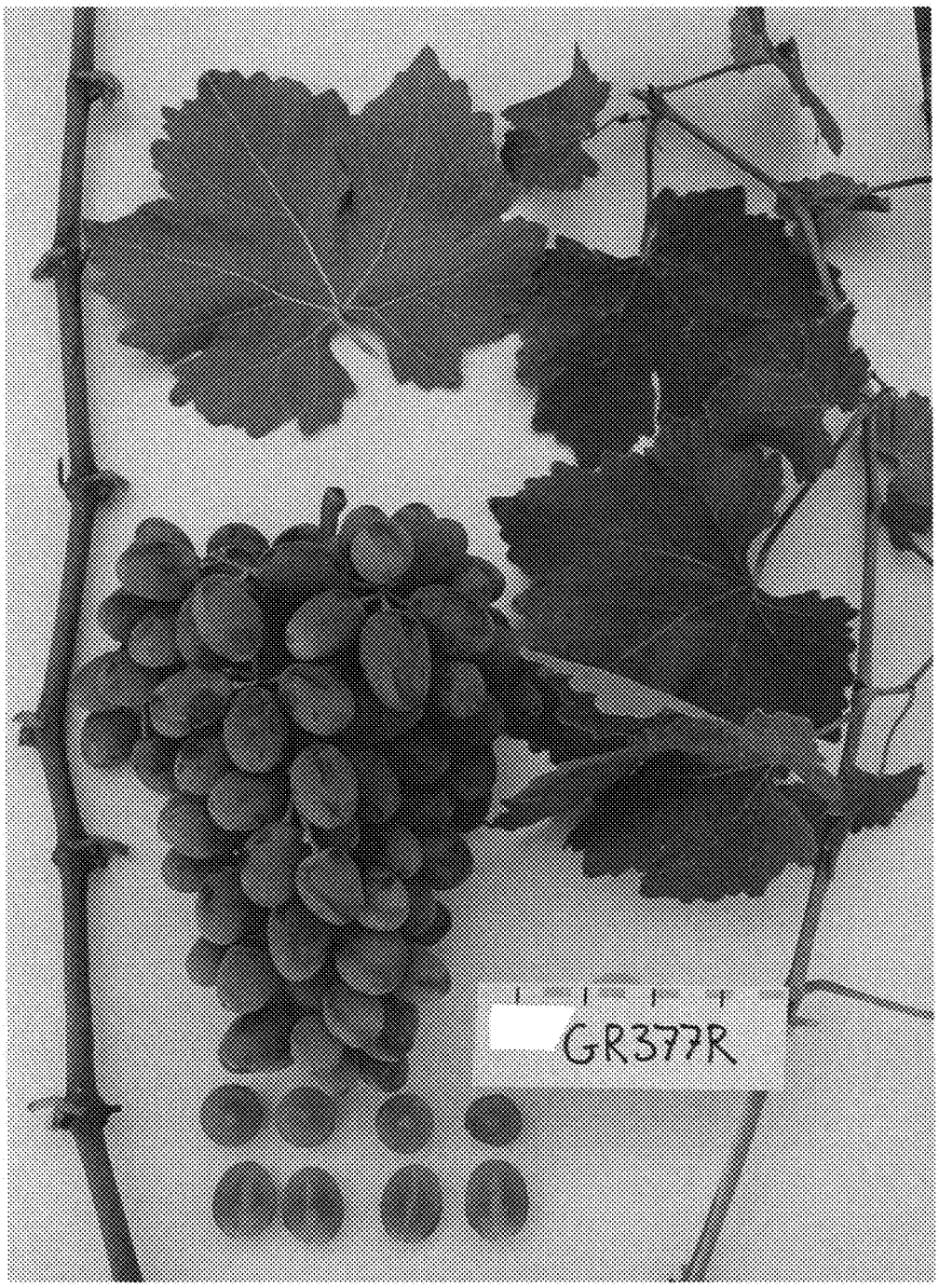
GR377R